US00PP35656P3

(12) United States Plant Patent
Olesen

(10) Patent No.: US PP35,656 P3
(45) Date of Patent: Feb. 20, 2024

(54) COMPACT FLORIBUNDA ROSE PLANT NAMED 'POULCAS065'

(50) Latin Name: *Rosa hybrida*
Varietal Denomination: Poulcas065

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 161 days.

(21) Appl. No.: 17/803,621

(22) Filed: Sep. 13, 2022

(65) Prior Publication Data

US 2023/0103286 P1 Mar. 30, 2023

(30) Foreign Application Priority Data

Feb. 9, 2023 (QZ) ..... PBR 2021/2368

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141, 149, 150, 151, 102, 107
CPC . A01H 5/02; A01H 5/00; A01H 5/674; A01H 5/749
See application file for complete search history.

(56) References Cited

PUBLICATIONS

Covo Register 4.2.46 for Rosa Poulcas065, retrieved on Nov. 8, 2022 at https://online.plantvarieties.eu/publicConsultationDetails?registerId=20212368&denomination=poulcas065, 2 pp. (Year: 2022).*
Floraland Poulsen Roser A/S 2020 retrieved on Nov. 14, 2022 at http://flora-land.ro/floraland/wp-content/uploads/2020/10/Floraland-Trandafir-si-clematis.pdf, 18 pp. (Year: 2020).*
Poulsen Roser A/S The Fairy-Tale Rose, retrieved on Nov. 15, 2022 at https://www.poulsenroser.dk/en/Roses/ShowProduct/76310, 2 pp. (Year: 2022).*
World Rose News The Newsletter of the World Federation of Rose Societies, retrieved on Nov. 8, 2022 at http://www.rosesocietyuruguay.com/pdf/World%20Rose%20News%20-%20August%202018.pdf, 2018, vol. 19, No. 2, 1-33. (Year: 2018).*

* cited by examiner

*Primary Examiner* — June Hwu

(57) ABSTRACT

A new garden rose plant of the Compact Floribunda class which has abundant, deep pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulcas065'.

This application claims priority to Plant Breeder's Rights Application Number 2021/2368, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulcas065', originated as a single seedling from the stated cross.

The new variety may be distinguished from its male pollen parent and female seed parent primarily by the following characteristics. The male pollen parent plant has red flowers while the new variety has deep pink flowers. The female seed parent plant has red flowers while the new variety has deep pink flowers.

The objective of the hybridization of this rose variety was to create a new and distinct variety with unique qualities, such as:

1. Uniform and abundant deep pink flowers;
2. Vigorous, but compact growth when propagated on its own roots; and
3. Exceptional disease resistance.

This combination of qualities is not present in previously available commercial cultivars of this type, known to the inventor, and distinguish 'Poulcas065' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulcas065' was selected in the spring of 2015 by the inventor as a single plant from the progeny of the aforementioned hybridization.

Asexual reproduction of 'Poulcas065' by rooted cuttings was first done by Mogens N. Olesen in the nursery in Fredensborg, Denmark in July, 2015. This initial and other subsequent asexual propagations conducted in controlled environments have demonstrated that the characteristics of 'Poulcas065' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas065'.

Specifically illustrated in FIG. 1 of the drawings are open flowers viewed from above and the side, flower petals detached revealing the sexual reproductive organs, and sepals detached revealing the shape of the receptacle.

Figure 1:
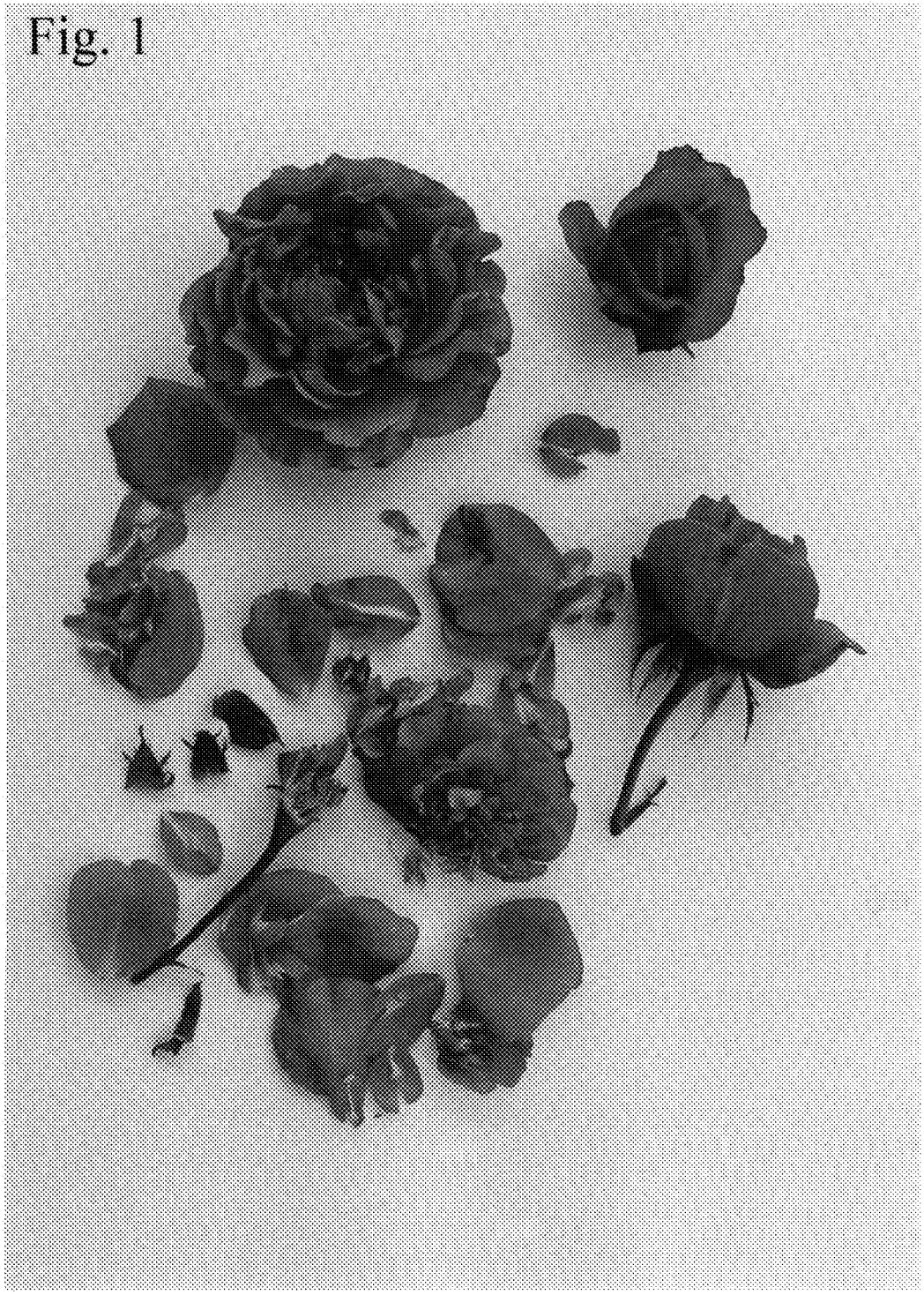
Figure 2:
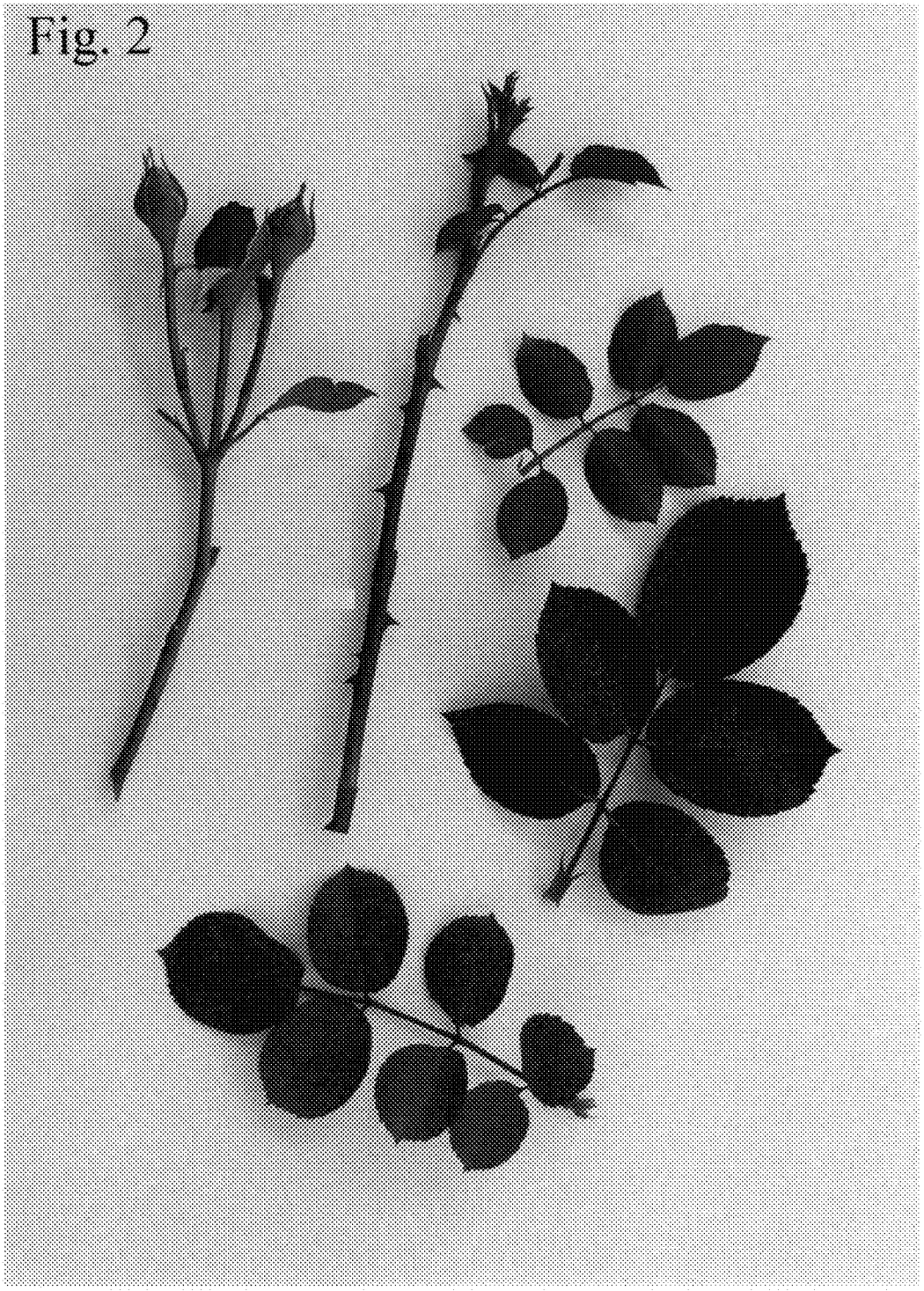

Specifically illustrated in FIG. 2 of the drawings are mature and juvenile leaves, bare stem revealing the shape and colour of prickles, and a cluster of flower buds attached to the branch. Plants shown are 2 years of age.

DETAILED DESCRIPTION OF THE VARIETY

The following is a description of 'Poulcas065', as observed in its growth outdoor in Odense Denmark. Observed plants are 18 months of age, and were grown on their own roots in 30 cm containers. Color references are made using The Royal Horticultural Society (London, England) Colour Chart, 2001, except where common terms of color are used.

For a comparison, several physical characteristics of the rose variety 'Poulcas061', U.S. Plant Pat. No. 32,346 are compared to the claimed plant, 'Poulcas065'. The claimed plant has 70 flower petals, while 'Poulcas061' has 35 to 40 petals. The claimed plant has a flower diameter of 85 mm while 'Poulcas061' has a flower diameter of 80 mm. The flower colour general tonality of the claimed plant is Red-Purple 61B, while the comparison variety 'Poulcas061' is Red-Purple Group 71B.

FLOWER AND FLOWER BUD

Blooming habit: Continuous.

Flower bud:

*Size.*—Upon opening, 25 mm in length from base of receptacle to end of bud. Bud diameter is 15 mm.

*Bud form.*—Urceolate.

*Sepal inner surface.*—Color: Yellow-Green Group 146D with strong intonations of Greyed-Purple Group 183A. Surface: Lightly pubescent.

*Sepal outer surface.*—Color: Yellow-Green Group 144A with strong intonations of Greyed-Purple Group 183A. Texture: Somewhat rough with stipitate glands.

*Sepal shape.*—Apex: Aristate. Base: Flat at union with receptacle.

*Sepal margin.*—Margins have moderate to strong foliaceous appendages on three of the five sepals.

*Sepal size.*—26 mm long, 11 mm wide.

*Receptacle.*—Texture: Smooth. Size: 10 mm in height, 9 mm wide. Color: Yellow-Green Group 144A with shades of Greyed-Red Group 181A. Shape: Funnel.

*Pedicel.*—Surface: Smooth. Length: About 40 mm. Diameter: 3 mm on average. Color: Yellow-Green Group 144A with intonations of Greyed-Red Group 181A. Strength: Strong.

*Peduncle.*—Length: On average 60 mm. Diameter: About 4 mm. Color: Yellow-Green Group 144A and Greyed-Red Group 181A. Texture: Smooth.

Flower bud development: Flower buds are borne in clusters of 3 to 5flower buds per stem, developing as a cyme.

Flower bloom:

*Fragrance.*—Moderate.

*Duration.*—The blooms have a duration on the plant of approximately 14 days. Petals fall cleanly away from plant after flowers have fully matured.

*Size.*—Flower diameter is 85 mm when open. Flower depth is 25 mm.

*Flower shape.*—Flowers form as a deep cup with outer petals reflexing outward.

*Shape of flower, side view.*—The upper portion is flat. The lower portion is partially flat to concave.

*Shape of the flower above view.*—Round.

Petalage: Under normal conditions, flowers have about 70 petals.

General tonality of flower: Open flowers are Red-Purple Group 61B. After flowers have fully opened the general tonality becomes Red-Purple Group N57C.

Petal color:

*Upon opening, outer petals.*—Upper surface: Red-Purple Group N57A with streaks of White 155A. At the basal point of attachment, a small basal petal spot of Yellow Group 4C. Lower surface: Red-Purple Group 61C with streaks of Red-Purple Group 62D. At the basal point of attachment, a small based petal spot of Yellow Group 4C.

*Upon opening, inner petals.*—Upper surface: Red-Purple Group N57A with streaks of Red-Purple Group 62D. At the basal point of attachment, a small basal petal spot of Yellow Group 4D. Lower surface: Red-Purple Group 58B with light streaks of Red-Purple Group 62D. At the basal point of attachment, a small basal petal spot of Yellow Group 4D.

*After opening, outer and inner petals.*—Upper surface: Red-Purple Group 61C with streaks of Red-Purple Group 62D. Lower surface: Red-Purple Group 61C with streaks of Red-Purple Group 62D. At the basal point of attachment, a small basal petal spot of Yellow Group 4D.

Petals:

*Petal reflex.*—Outer petals partially reflexed.

*Margin.*—Irregular with numerous clefts and strong undulations.

*Shape.*—Broad and elliptic. Apex shape: Rounded. Base shape: Obtuse and acute.

*Size.*—About 35 mm (l)×44 mm (w).

*Texture.*—Somewhat rugose.

*Thickness.*—Above average.

Petaloids:

*Size.*—20 to 30 mm (l) by 10 mm (w).

*Quantity.*—About 35.

*Shape.*—Elliptical with an acute base and rounded apices. Many petaloids are fused or attached to the stamens.

*Color.*—Red-Purple Group N57A with streaks of Red-Purple Group 62D on the upper and lower surface.

Reproductive flower parts:

*Pollen.*—None observed.

*Anthers.*—Size: 3 mm in length. Color: Yellow-White Group 158B. Quantity: 70 on average.

*Filaments*.—Color: Green-White Group 157D. Length: 5 mm.

*Pistils*.—Length: 4 mm. Quantity: Varying from 60 to 150.

*Stigmas*.—Color: Green-White Group 157A.

*Styles*.—Color: Green-White Group 157A.

*Location of stigmas*.—Inferior in location relative to the length of the filaments and the height of the anthers.

*Hips*.—None Observed.

PLANT

Plant growth: Upright, bushy. Plants are 40 cm in height, and 55 cm wide.

Stems:

*Color of juvenile growth*.—Yellow-Green Group 146B with intonations of Greyed-Purple Group 183B.

*Color of mature growth*.—Yellow-Green Group 146B.

*Length*.—Canes are about 20 cm from the base of the plant to the flowering portion.

*Diameter*.—About 5 mm.

*Internodes*.—On mature canes about 40 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 5 mm.

*Shape*.—Upper portion is linear. Lower portion is concave.

*Color*.—Juvenile prickles: Greyed-Purple Group 183A. Mature prickles: Greyed-Orange Group 166B.

Plant foliage:

*Compound leaf*.—165 mm (l)×120 mm (w).

*Quantity*.—2 leaves per 10 cm of stem on average.

*Leaf bearing angle to the stem*.—45 degrees.

*Color of juvenile foliage*.—Upper side: Yellow-Green Group 146B with intonations of Greyed-Purple Group 187B. Lower side: Yellow-Green Group 146B with intonations of Greyed-Purple Group 187B.

*Color of mature foliage*.—Upper side: Yellow-Green Group 147A. Lower side: Yellow-Green Group 147B.

Plant leaves and leaflets:

*Stipules*.—Size: 16 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 35 mm. Diameter: 2 mm. Upper surface color: Greyed-Orange Group 166A. Lower surface color: Yellow-Green Group 144A.

*Rachis*.—Length: 50 mm. Upper surface color: Yellow-Green Group 146A with intonations of Greyed-Orange Group 166A. Lower surface color:

*Leaflet*.—Quantity: Normally 5 leaflets. Margins: Serrated. Size: Terminal leaflets are about 70 mm long, 48 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcas065' substantially as described and illustrated herein.

* * * * *